United States Patent
Laabs et al.

(10) Patent No.: US 6,842,649 B2
(45) Date of Patent: Jan. 11, 2005

(54) SNAP-SPIN LEAD ASSEMBLY AND METHOD THEREFOR

(75) Inventors: Matthew Laabs, San Juan, PR (US); Scott M. Partridge, Shoreview, MN (US); Jon Schell, Brooklyn Park, MN (US); Walt Laroche, Crystal, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 402 days.

(21) Appl. No.: 10/017,266

(22) Filed: Dec. 14, 2001

(65) Prior Publication Data

US 2003/0114907 A1 Jun. 19, 2003

(51) Int. Cl.⁷ .............................................. A61N 1/05
(52) U.S. Cl. ........................................................ 607/127
(58) Field of Search .............................. 607/115, 116, 607/119, 122, 127; 606/108; 600/373, 374, 375, 381

(56) References Cited

U.S. PATENT DOCUMENTS

| | | | |
|---|---|---|---|
| 4,967,766 A | 11/1990 | Bradshaw | 128/785 |
| 5,129,404 A | 7/1992 | Spehr et al. | 128/785 |
| 5,228,455 A | 7/1993 | Barcel | 128/785 |
| 5,447,534 A | 9/1995 | Jammet | 607/127 |
| 5,514,172 A | 5/1996 | Mueller | 607/122 |
| 5,628,779 A | 5/1997 | Bornzin et al. | 607/123 |
| 5,910,150 A | 6/1999 | Saadat | 606/159 |
| 5,931,848 A | 8/1999 | Saadat | 606/167 |
| 5,941,893 A | 8/1999 | Saadat | 606/180 |
| 5,968,085 A | 10/1999 | Morris et al. | 607/116 |
| 6,142,446 A | 11/2000 | Leinsing | 251/149.1 |
| 6,324,434 B2 * | 11/2001 | Coe et al. | 607/119 |
| 6,463,334 B1 | 10/2002 | Flynn et al. | 607/127 |
| 6,501,990 B1 * | 12/2002 | Sundberg et al. | 607/122 |
| 2003/0040787 A1 * | 2/2003 | Flynn et al. | 607/122 |
| 2003/0083727 A1 | 5/2003 | Casavant et al. | 607/122 |
| 2003/0181850 A1 | 9/2003 | Diamond et al. | 604/30 |

FOREIGN PATENT DOCUMENTS

WO WO-00/04948 2/2000 ............ A61N/1/05

* cited by examiner

*Primary Examiner*—George Manuel
(74) *Attorney, Agent, or Firm*—Schwegman, Lundberg, Woessner & Kluth, P.A.

(57) ABSTRACT

A lead assembly having a push-extendable active fixation mechanism. As the terminal end of the lead is pushed, the active fixation element extends from the lead body to a predetermined extension length. Optionally, a seal is formed at the distal end when the terminal is pushed and the terminal moves axially. A further option includes providing a snap fit connection with the terminal when the terminal end is pushed and the active fixation element is fully extended.

36 Claims, 7 Drawing Sheets

SNAP-SPIN LEAD ASSEMBLY AND METHOD THEREFOR

TECHNICAL FIELD

The present invention relates to the field of insertable or implantable materials or devices in which the material or device is secured into the tissue of a patient through a helical or screw element which is secured into tissue or the like.

BACKGROUND

Electrodes have been used to stimulate contraction of the heart or to reverse certain life-threatening arrhythmias, where electrical energy is applied to the heart via the electrodes to return the heart to normal rhythm. Electrodes have also been used to sense and deliver pacing pulses to the atrium and ventricle. Cardiac pacing may be performed by a transvenous method or by electrodes implanted directly onto the epicardium. For transvenous pacing systems, a lead having an electrode is positioned in the right ventricle and/or in the right atrium through a subclavian vein, and the proximal electrode terminals are attached to a pacemaker which is implanted subcutaneously.

Some lead designs have "floating" electrodes or electrodes which are not attached to the endocardial wall of the heart. The floating electrodes lay in the blood pool or against the endocardial wall of the heart and the electrode may move slightly within the heart. Since the location of floating electrodes is not fixed with respect to the endocardial wall, the electrical performance of these electrodes varies and is generally less than optimal. Both the electrical sensing capability as well as the pacing delivery capability of such electrodes are suboptimal. The pacing parameters of such a floating electrode are also suboptimal. In addition, the floating electrodes can require increased voltage which unnecessarily drains the battery.

As an alternative to floating electrodes, leads have been provided with passive fixation elements that affix the electrode to the endocardial wall over time. With passive fixation elements, it can be difficult to determine whether the lead will affix in the location at which it is implanted.

Active fixation elements, such as a helix, have also been provided with distal ends of leads which allow a lead to be affixed to the endocardial wall. A lead with an active fixation element may be inserted into a patient by a number of different medical procedures. The less invasive or traumatic the procedure, the more desirable is that procedure. For example, although the electrodes may be inserted by open chest surgery, the delivery of the electrode through catheterization techniques through arteries or veins is much more preferred. The difficulties involved with passing a sharp element through the vasculature of a patient can be readily appreciated, especially where the path can be tortuous or partially clogged with deposits. To avoid damage to the patient, the GUIDANT™ Sweet-Tip™ Model 4269 and the GUIDANT™ Sweet Pico Tip bipolar endocardial leads provide a mannitol cap over the helical element in the lead. The mannitol cap provides a protective cover for the helical element which prevents the point of the helical element from scraping or puncturing interior walls of the vasculature or other tissue during introduction of the element to the patient. The physician must wait for the mannitol cap to dissolve after the lead is implanted into the heart before the helical element can be affixed to tissue of the patient.

Other formats for delivering helical or barbed elements to secure an electrode into contact with appropriate tissue have utilized securing elements which are in a retracted position within the end of the delivered electrode. The retracted element is rotated and advanced into an exposed and operative position after positioning the distal end of the electrode element within the heart of a patient. Advancement and exposure of the retracted element may be effected by winding or screwing the helical element with a stylet disposed within the lead, or with the pin cap. As the stylet or the cap is rotated, however, the active fixation element may jump out of the end of the lead due to friction, for example, from a buildup of tissue or blood within the lead. Unexpected movement of the helix leads to potential tissue damage, and longer implant times. In addition, it is difficult for the physician to determine how many turns to the stylet or pin cap are necessary to fully advance the helix from the lead.

SUMMARY

The lead assembly provided herein overcomes the above-stated problems and provides a lead with helical advancing structure that allows for the physician to fully advance the active fixation element quickly and with certainty, and without having to apply torque thereto.

A lead assembly includes a flexible lead body extending from a proximal end to a distal end, where the lead body has one or more conductors disposed therein. The lead assembly further includes at least one electrode electrically coupled with at least one conductor, and a connector assembly coupled with the proximal end of the flexible lead body, the connector assembly including a terminal movable between a first axial position and a second axial position relative to the lead body after the connector assembly is coupled with the flexible lead body. In addition, the lead assembly includes an active fixation assembly coupled at the distal end of the flexible lead body, the active fixation assembly placed in a compression fit with the distal end of the lead body when the terminal is placed in the second axial position. An inner assembly is coupled with the terminal and the active fixation assembly, where the inner assembly is coupled between the terminal and the active fixation assembly.

Several options for the lead assembly are as follows. In one option, for instance, the lead assembly further includes a seal disposed at the distal end of the lead body, and the active fixation assembly has a compression fit with the seal at the distal end of the lead body. In another option, the terminal has a snap fit coupling with a terminal housing when the terminal is placed in the second axial position. In yet another option, the active fixation assembly includes a fixation helix extending outside of the lead body when the terminal is in the second axial position, and optionally the entire fixation helix is disposed within the lead body when the terminal is in the first axial position. Optionally, the active fixation assembly abuts against a stop when the terminal is placed in the second axial position. In another option, a clip is coupled with the terminal, where the clip prevents movement of the terminal from the first axial position to the second axial position.

In another embodiment, a lead assembly includes a flexible lead body extending from a proximal end to a distal end, where the lead body has one or more conductors disposed therein. An electrode assembly, including at least one electrode, is electrically coupled with at least one conductor, and a connector assembly is coupled with the proximal end of the flexible lead body. The connector assembly has a terminal that is movable between a first axial position and a second axial position relative to the lead body after the connector assembly is coupled with the flexible lead body.

The terminal is coupled with a terminal housing in a snap fit connection when the terminal is placed in the second position. The lead assembly further includes an active fixation assembly that is coupled at the distal end of the flexible lead body. An inner assembly is coupled with the terminal and the active fixation assembly, where the inner assembly is coupled between the terminal and the active fixation assembly. The active fixation assembly has a fixation helix which extends outside of the lead body when the terminal is in the second axial position.

Several options for the lead assembly are as follows. For instance, in one option, the active fixation assembly is placed in a compression fit with the distal end of the lead body when the terminal is placed in the second axial position. In another option, the terminal is prevented from being placed in the first position once the terminal is placed in the second position. The lead assembly, in another option, further includes a clip coupled with the terminal, where the clip prevents movement of the terminal from the first axial position to the second axial position. In another option, the inner assembly includes an elongate braided member. In yet another option, the terminal pin is rotatable relative to the lead body after the terminal is placed in the second axial position, and rotation of the terminal pin causes the fixation helix to rotate. The lead further includes, in another option, a stylet disposed within the lead body and a tool member disposed over the stylet, where the tool member includes one or more planar members disposed substantially traverse to a longitudinal axis of the lead body. Axial movement of the tool member causes axial movement to the inner assembly.

In another embodiment, a method is provided herein. The method includes pushing on a proximal end of a lead assembly, where the lead assembly has a flexible lead body extending from a proximal end to a distal end, and the lead body including one or more conductors disposed therein. The lead assembly further includes an electrode assembly with at least one electrode electrically coupled with at least one conductor, and a connector assembly coupled with the proximal end of the flexible lead body. The connector assembly has a snap fit terminal having a first position and a second position. The lead assembly further includes an active fixation assembly coupled at the distal end of the flexible lead body. The method further includes moving the active fixation assembly axially from an unexposed position to an exposed position, and moving the active fixation assembly is conducted without applying torque to the terminal or the active fixation assembly. In addition, the method includes placing a base of the active fixation assembly in a compression fit with the distal end of the lead body when the active fixation assembly is moved to the exposed position.

Several options for the method are as follows. For instance, in one option, the method further includes removing a clip from the proximal end of the lead body, wherein the clip prevents the terminal from moving between the first position and the second position. In another option, the method includes snap-fittedly coupling the terminal with a terminal housing when the terminal is placed in the second position. The method includes, in another option, rotating the lead body and thereby rotating the active fixation assembly, or optionally sealing the distal end of the lead body when the active fixation assembly is placed in the exposed position.

In another embodiment, a method comprises pushing on a proximal end of a lead assembly, where the lead assembly has a flexible lead body extending from a proximal end to a distal end, and the lead body has one or more conductors disposed therein. The lead assembly further includes an electrode assembly with at least one electrode electrically coupled with at least one conductor, and a connector assembly coupled with the proximal end of the flexible lead body. The connector assembly includes a terminal movable between a first axial position and a second axial position relative to the lead body after the connector assembly is coupled with the flexible lead body. In addition, the terminal is coupled with a terminal housing in a snap fit connection when the terminal is placed in the second position. The lead assembly further includes an active fixation assembly coupled at the distal end of the flexible lead body, the active fixation assembly including a fixation helix. The method further includes moving the terminal from the first axial position to the second axial position, placing the terminal in a snap fit connection with a terminal housing, and pushing the fixation helix from a retracted position to an extended position.

Several options for the method are as follows. For instance, in one option, the method further includes placing a base of the active fixation assembly in a compression fit with the distal end of the lead body and sealing the lead body when the active fixation assembly is moved to the exposed position. In another option, the method further includes rotating the lead body and thereby rotating the active fixation assembly. In yet another option, the method further includes removing a clip from the proximal end of the lead body, wherein the clip prevents the terminal from moving between the first axial position and the second axial position. Additionally, in another option, the method further includes rotating the terminal and thereby rotating the active fixation assembly. In yet another option, the method further includes, disposing a stylet within the lead body, placing a tool member around the stylet, and pushing on the tool member.

The lead assembly allows for an implant of a lead with the helix disposed within the lead body, which assists in preventing trauma to passages from the helix. In addition, the lead assembly does not require the use of a specialized stylet, which provides a time savings as switching in a specialized stylet involves extra time at implant. In addition, the specialized stylet is disliked by some physicians, and may become a distraction to some physicians. The snap fit terminal assists in locking the fixation assembly in an extended position, eliminating the need to torque the fixation assembly into the extended position, saving time and the uncertainty of whether or how far the fixation assembly has been extended. In addition, the snap fit positively indicates to the physician when the helix has been fully extended, and further assists in preventing the helix from inadvertently retreating into the lead body. The extension of the helix can be done quickly and without trauma to tissue, as opposed to having to wait for a coating to dissolve, and without the uncertainty of whether the coating has fully dissolved, or dissolved sufficiently to affix the helix to tissue.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
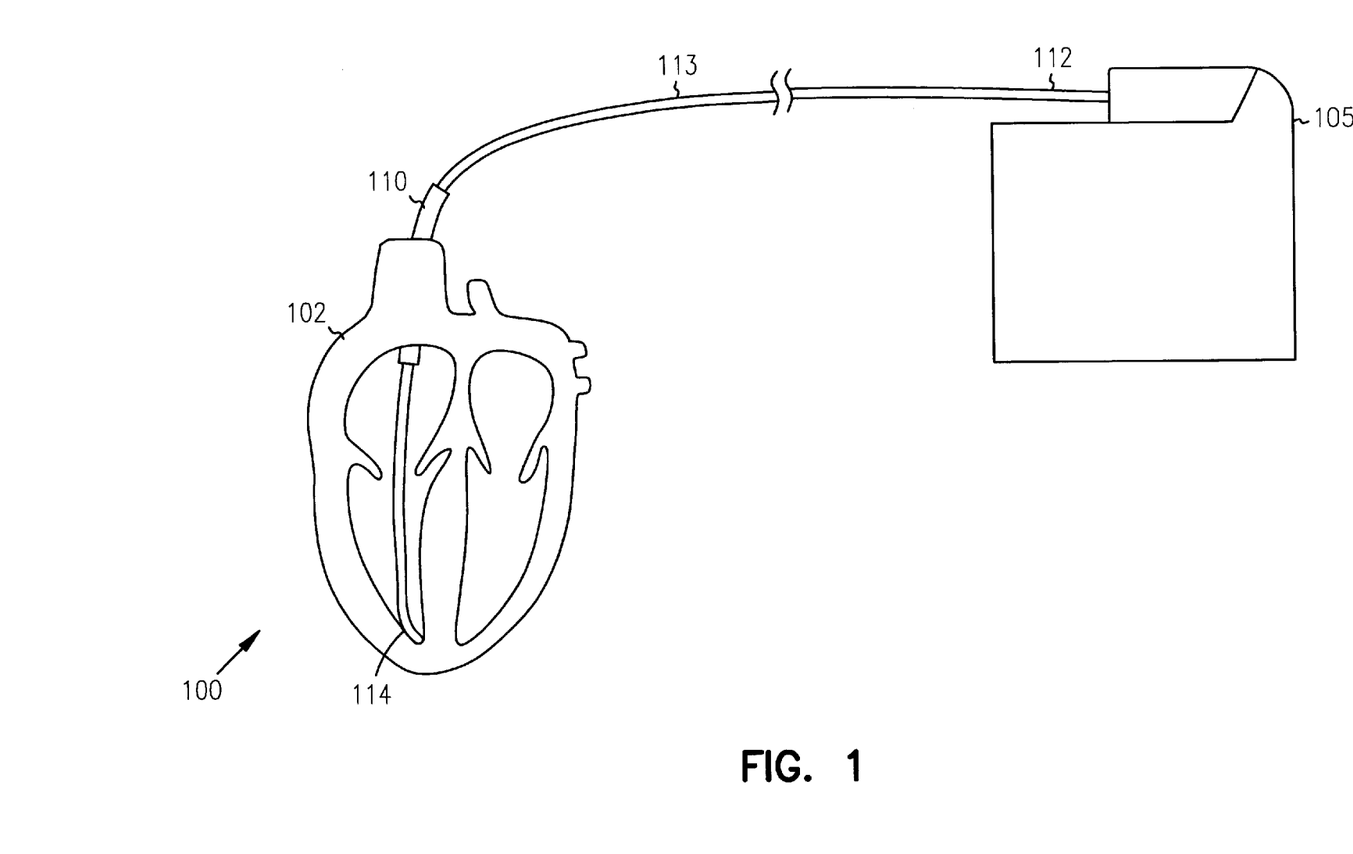
FIG. 1 is a block diagram illustrating a system for delivering and/or receiving and/or detecting signals to and from the heart constructed in accordance with one embodiment.

An extendable and retractable lead 110 and lead system 100 are illustrated in FIG. 1. FIG. 1 is a block diagram of a system 100 for delivering and/or receiving electrical pulses or signals to stimulate and/or sense the heart 102. The system 100 includes a pulse generator 105 and a lead 110. The pulse generator 105 includes a source of power as well as an electronic circuitry portion. The pulse generator 105 is a battery-powered device which generates a series of timed electrical discharges or pulses. The pulse generator 105 is generally implanted into a subcutaneous pocket made in the wall of the chest. Alternatively, the pulse generator 105 is placed in a subcutaneous pocket made in the abdomen, or in other locations.

The lead 110 includes a flexible lead body 113 which extends from a proximal end 112, where it is coupled with the pulse generator 105, as further discussed below. The lead 110 extends to a distal end 114, which is coupled to or near a portion of a heart 102, when implanted. The distal end 114 of the lead 110 includes at least one electrode 116 (FIG. 3) which electrically couples the lead 110 with the heart 102. At least one electrical conductor 118 (FIG. 3) is disposed within the lead 110 and extends from the proximal end 112 to the distal end 114 of the lead 110. The at least one electrical conductor 118 electrically couples the electrode 116 with the proximal end 112 of the lead 110. The electrical conductors carry electrical current and pulses between the pulse generator 105 and the electrode 116.

Figure 2:
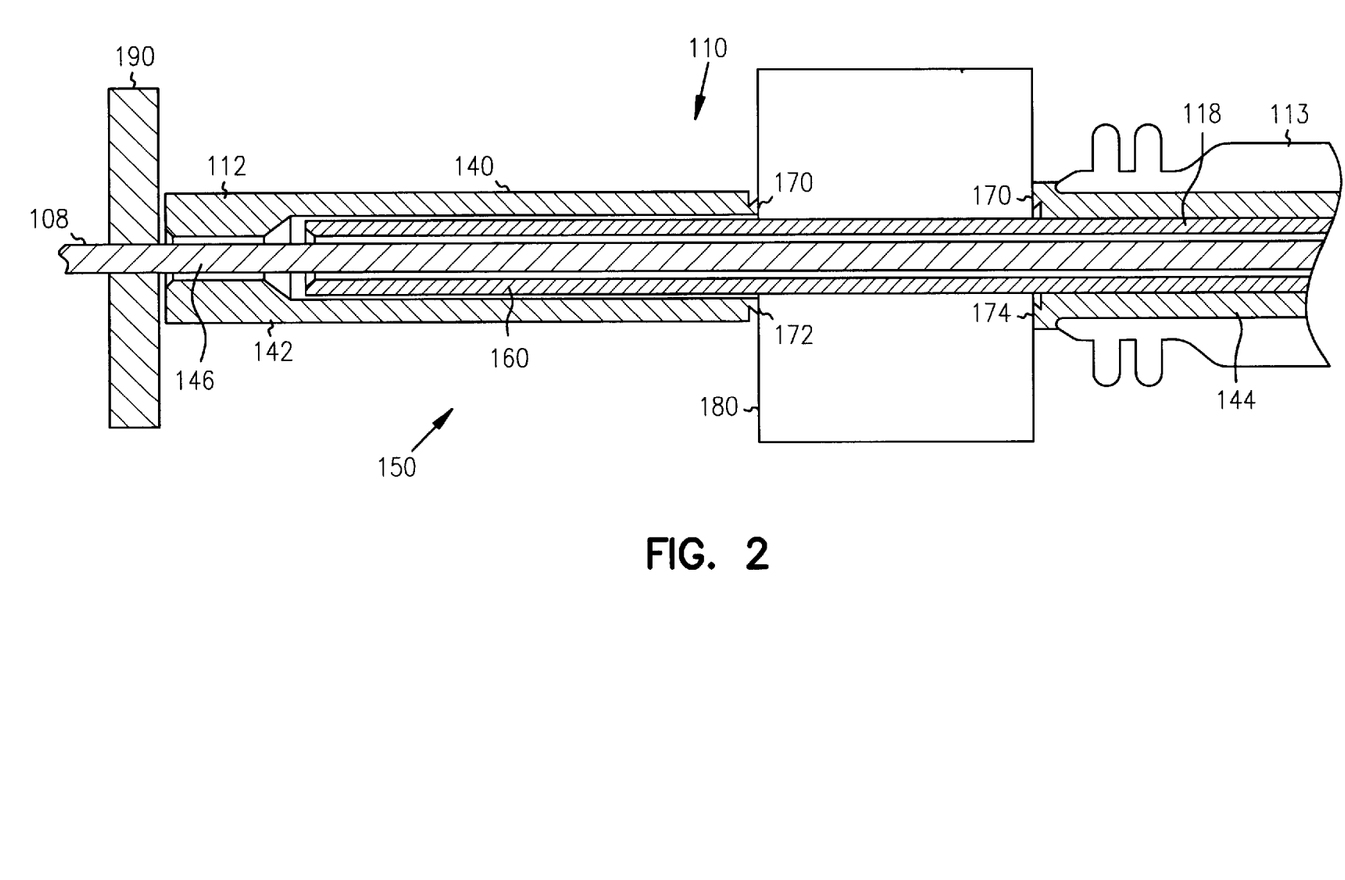
FIG. 2 is a cross sectional view illustrating a proximal portion of a lead assembly as constructed in accordance with one embodiment.
Figure 3:
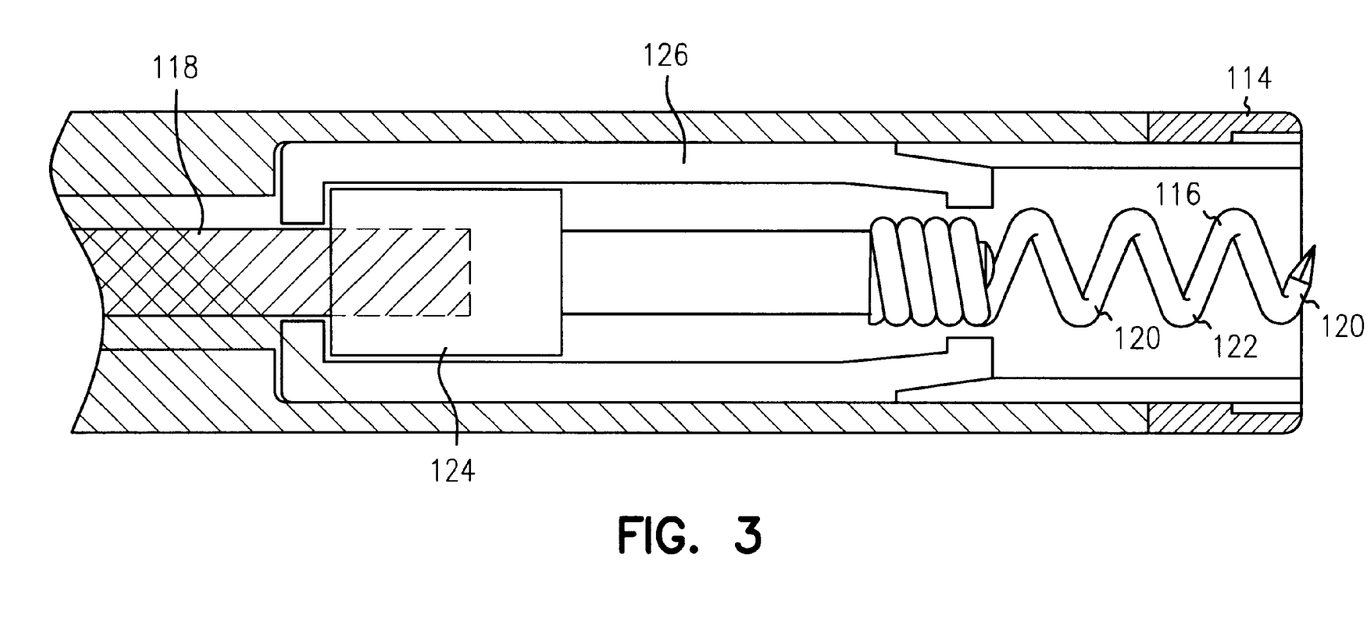
FIG. 3 is a cross sectional view illustrating a distal portion of a lead assembly as constructed in accordance with one embodiment.
Figure 4:
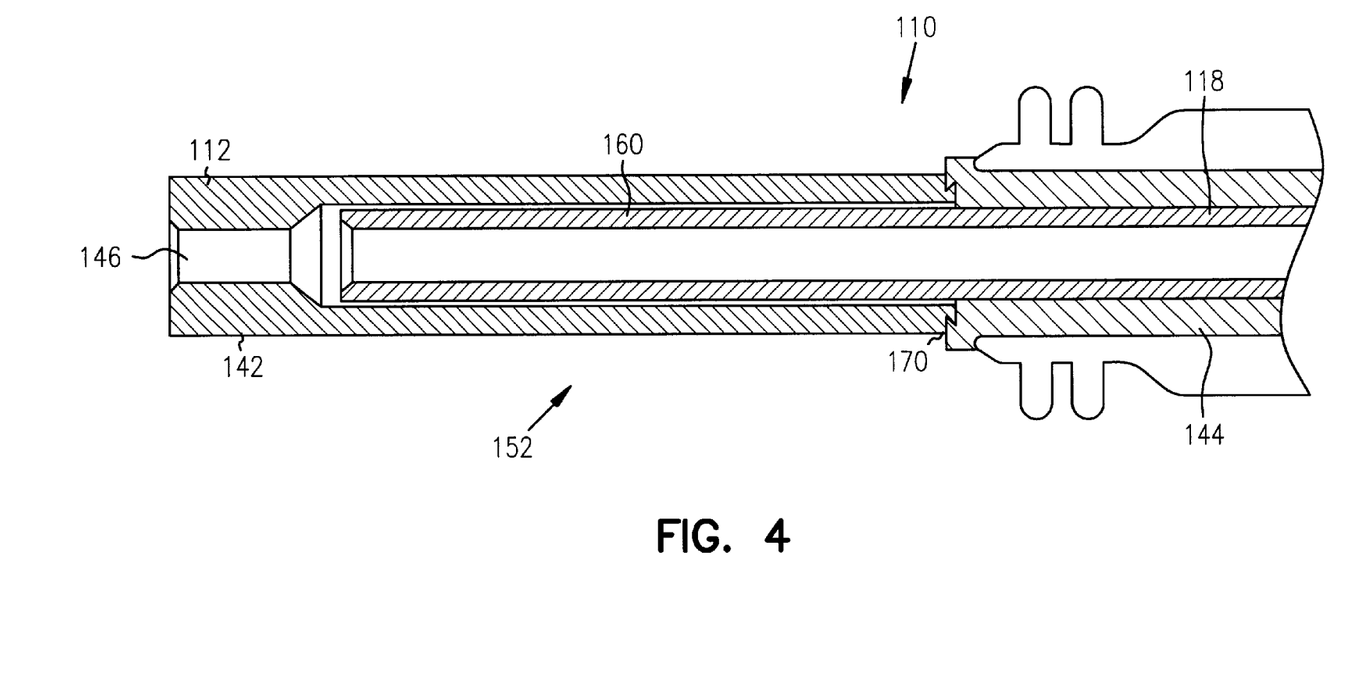
FIG. 4 is a cross sectional view illustrating a proximal portion of a lead assembly as constructed in accordance with one embodiment.
Figure 5:
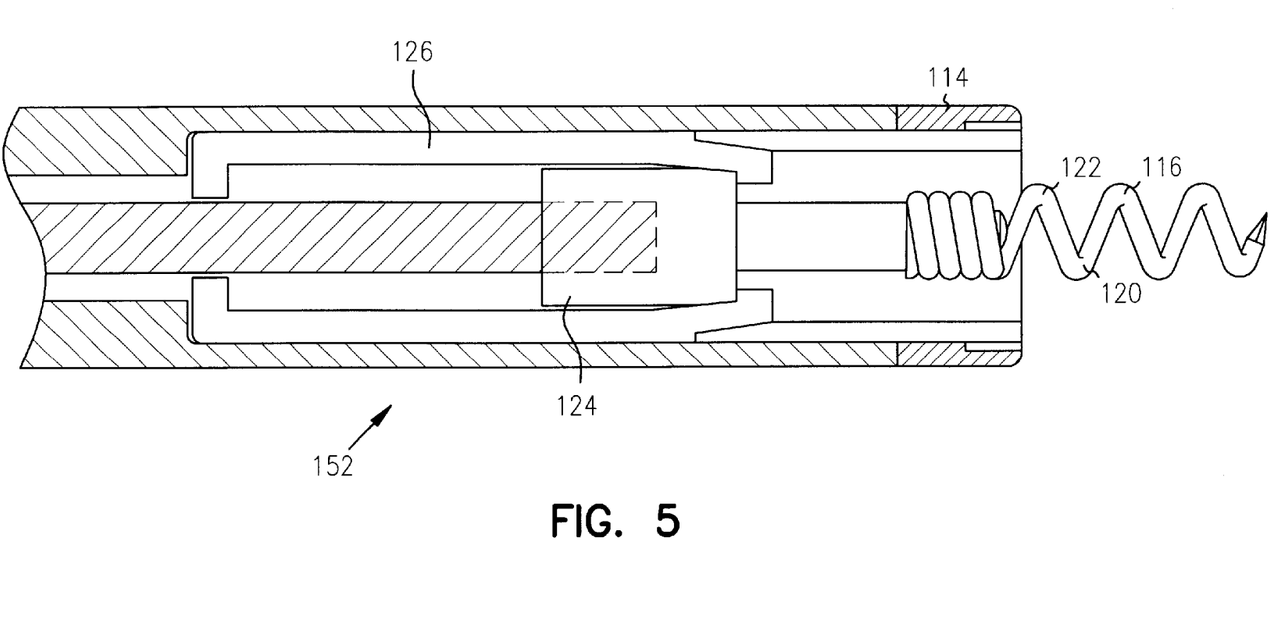
FIG. 5 is a cross sectional view illustrating a distal portion of a lead assembly as constructed in accordance with one embodiment.

FIGS. 2–5 illustrate the lead 110 in greater detail, where FIGS. 2 and 3 illustrate the lead 110 in a retracted position and FIGS. 4 and 5 illustrate the lead 110 in an extended position. The electrode 116 includes a fixation helix 120 which allows for the distal end 114 of the lead 110 to be affixed to the heart 102 (FIG. 1). The fixation helix 120 is mechanically and electrically coupled with an electrode base 124.

FIG. 2 illustrates a proximal end 112 of the lead 110. The proximal end 112 includes connector assembly 140 which includes a terminal 142 and a terminal housing 144. Within the terminal 142 is a lumen 146 which allows for instruments to be received therein. For example, a stylet 108 is optionally disposed within the lumen 146, where optionally the stylet can be used to push the inner assembly. However, it should be noted that a specialized stylet is not necessary for the extension and retraction of the helix, as further discussed below. Optionally, the lumen 146 extends throughout the entire lead 110.

The connector assembly 140 further includes a snap-fit coupling 170. For instance, the terminal 142 includes a projection 172 which fits within a recess 174 of a terminal housing 144 when the terminal 142 is a moved from a first axial position 150, as shown in FIG. 2, to a second axial position 152, as shown in FIG. 4. It should be noted that the projection 172 is optionally placed on the terminal housing 144, and the recess 174 is disposed on the terminal 142, or that other snap-fit coupling features can be incorporated herein, and are considered within the scope of the invention.

The terminal 142 is coupled with an inner assembly 160 which allows for the terminal 142 to move within the lead 110. Specifically, the inner assembly 160 allows for the terminal 142 to move axially along the lead 110. A clip 180, in one option, is coupled with the inner assembly 160. The clip 180 is shown in greater detail in FIG. 6A.

Figure 6A:
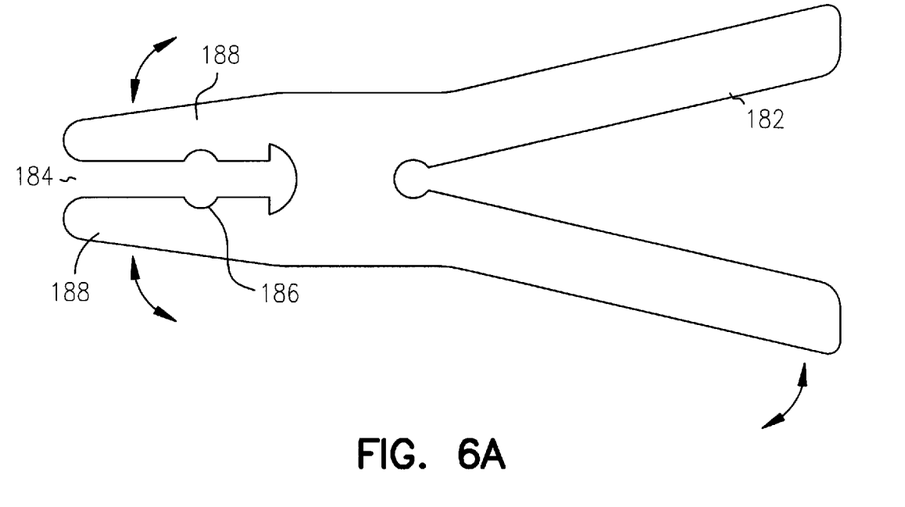
FIG. 6A is a side elevational view illustrating a clip constructed in accordance with one embodiment.

The clip 180 includes a handle 182 which is operatively coupled with arms 188, which have an opening 184 therein. Within the opening 184 along a surface therein, is a second opening 186. The second opening 186 is sized to fit with the inner assembly 160 (FIG. 2). For example, the second opening 186 includes a circular opening which is larger than the opening 184, where the second opening 186 fits around an outer diameter of the inner assembly 160 (FIG. 2). As the physician squeezes the handle 182, the arms 188 open and opening 184 is made larger to accept the inner assembly 160 (FIG. 2). The clip 180, when disposed around the inner assembly, prevents the terminal 142 (FIG. 2) from moving relative to the lead body 113 (FIG. 2). This allows for the prevention of inadvertently moving the terminal and also the active fixation elements prior to a time that is desired by the physician.

Figure 6B:
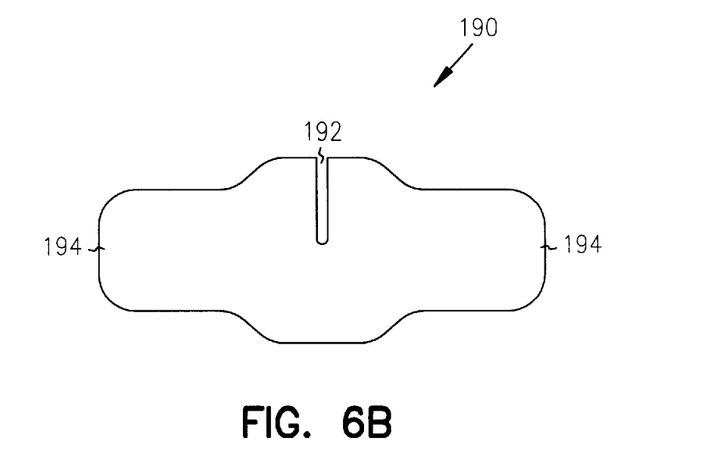
FIG. 6B is a top plan view illustrating a tool member constructed in accordance with one embodiment.

A tool member 190 is optionally coupled with the optional stylet 108. The tool member 190, shown in greater detail in FIG. 6B, further facilitates axially moving the active fixation assembly without having to torque an element of the lead or a separate tool such as a specialized stylet. The tool member 190 includes a slot 192 that is sized and positioned to allow the stylet 108 to pass therethrough. The slot 192, however, is less wide than the outer diameter of the terminal. The tool member 190 further includes one or more planar members 194. The tool member 190 is disposed over the stylet 108 such that the one or more planar members 194 are disposed substantially transverse to a longitudinal axis of the lead body (FIG. 2). The tool member 190 is pushed against the terminal 142 to place an axial force along the inner assembly and to the active fixation assembly, and is optionally used to move the active fixation assembly from a first recessed position to a second extended position. The planar members 194 provide a greater surface area to which the axial force is applied, easing use of the lead 110.

Referring to FIG. 2, the terminal 142 is movable with respect to the lead body 113 after the lead 110 has been assembled, and has been implanted into a patient. The terminal 142 is movable from a first axial position 150 to a second axial position 152 (FIG. 4) which moves an active fixation assembly 120 at the distal end 114 from a retracted position as shown in FIG. 3, to an extended position as shown in FIG. 5. Referring again to FIG. 3, the distal end 114 of the lead body 113 includes an electrode base 124 which is movably disposed within a bushing 126. The bushing 126 is sized and configured to receive the electrode base 124 and at least a portion of the inner assembly 160 therein. The bushing 126, in one option, is formed of poly ether ether ketone, for example, by molding. The electrode base 124 is coupled with the inner assembly 160, for example by welding. The electrode base 124 and the inner assembly 160 are coupled with the active fixation assembly 120 such that the movement of the terminal 142 causes movement of the electrode base 124 and also the active fixation assembly 120. A surface 127 of the bushing 126 forms a stop for the base 124, and assists in preventing over-extension of the helix.

FIG. 4 illustrates the proximal end 112 of the lead 110 and the second axial position 152. Once the clip 180 (FIG. 2) has been removed from the inner assembly 160, the terminal 142 can be placed in the second axial position 152. Optionally, the terminal 142 is snap-fittedly coupled with the terminal housing 144. The snap-fit coupling 170 is beneficial to the physician as it indicates to the physician when the fixation helix has been fully and properly extended from the lead 110. In addition, the snap-fit coupling 170 prevents the active fixation assembly 120 from being inadvertently retracted back into the lead 110. To place the terminal in the second axial position 152, the physician pushes on the proximal end 112 of the terminal 142 until the terminal 142 abuts the terminal number 144, for instance, in a snap-fit coupling. It should be noted that the terminal 142 is moved from the first axial position 150 to the second axial position 152 after the lead 110 has been placed within a heart of a patient.

FIG. 5 illustrates the distal end 114 of the lead 110 once the terminal 142 (FIG. 4) has been placed in the second axial position 152. In the second axial position, the fixation helix 122 is extended from the distal end 114 of the lead 110. In one option, the fixation helix 122 is entirely extended from the lead body 113 in this second axial position 152. In another option, the electrode base 124 forms a compression fit with the bushing 126 when the terminal 142 (FIG. 4) is placed in the second axial position. The compression fit assists in indicating to the physician when the helix has been properly extended. In another option, a seal is formed once the electrode base 124 is placed in compression fit with the bushing 126. In addition, having the compression fit in addition to the snap-fit coupling achieves superior stability. The seal, for example formed by the compression fit, assists in preventing any blood from entering the inner lumen and interfering with assemblies within the lead 110. In another option, the electrode base 124 and the bushing 126 include snap-fit features, and the electrode base 124 and the bushing are snap-fittedly coupled together, and optionally forming a seal thereby. A snap fit connection would occur at the proximal end and/or the distal end of the lead 110.

Figure 7:
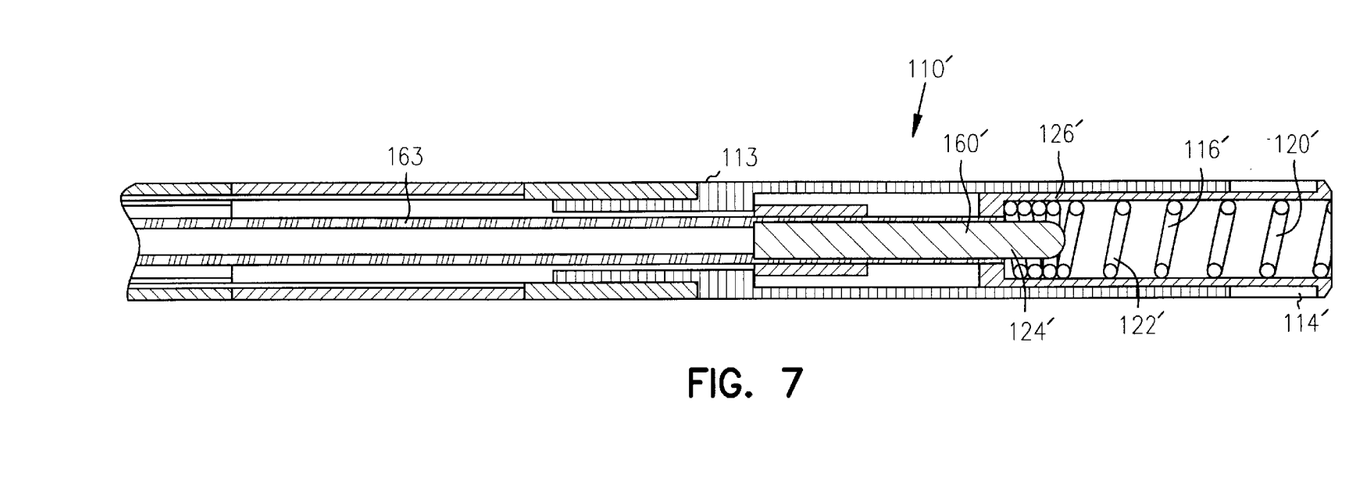
FIG. 7 is a cross sectional view illustrating a distal portion of a lead assembly as constructed in accordance with one embodiment.
Figure 8:
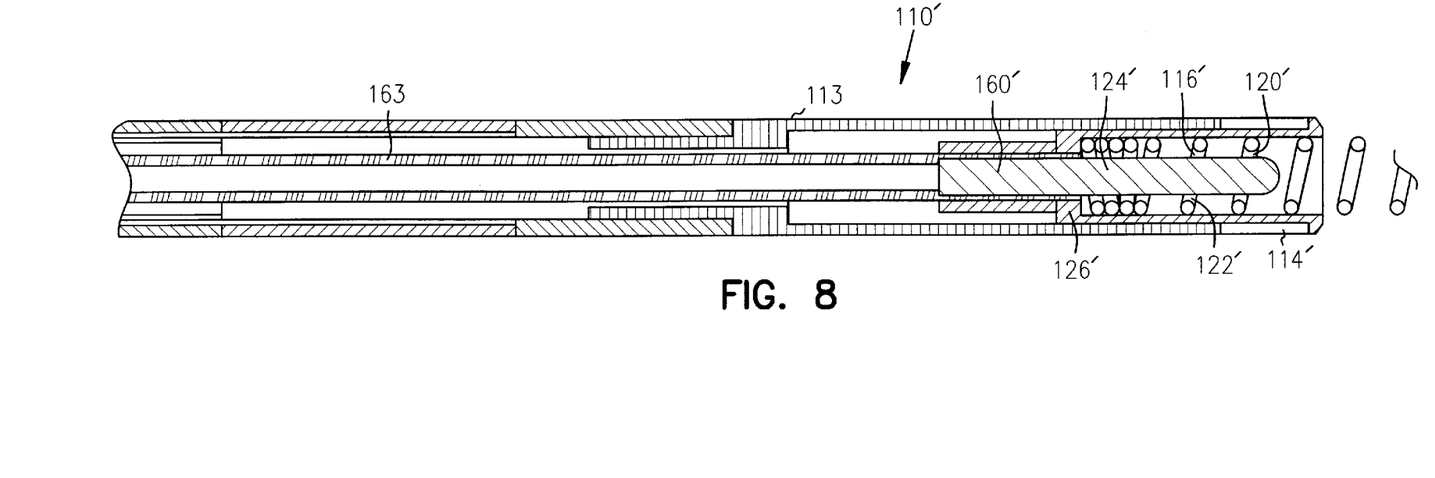
FIG. 8 is a cross sectional view illustrating a distal portion of a lead assembly as constructed in accordance with one embodiment.

FIGS. 7 and 8 illustrate another embodiment of the lead 110'. The lead 110' has a proximal portion as illustrated in FIGS. 2 and 4, and as described above, and is operable within the system as shown in FIG. 1 and as described above. FIG. 7 illustrates the lead 110' in a retracted position, and FIG. 8 illustrates the lead 110' in an extended position. The lead 110' includes an electrode 116', that has a fixation helix 120', where the fixation helix 120' allows for the distal end 114' of the lead 110' to be affixed to the heart 102 (FIG. 1).

The terminal 142 (FIG. 2) is coupled with an inner assembly 160' which allows for the terminal 142 (FIG. 2) to move within the lead 110'. Specifically, the inner assembly 160' allows for the terminal 142 (FIG. 2) to move axially along the lead 110', and allows for axial force to be transmitted to other components coupled with the inner assembly 160', such as the fixation helix, as further discussed below. In one option, the inner assembly 160' includes a braided component, for instance, an elongate braided conductor 163. The braided component is disposed between the active fixation assembly and the terminal. The braided component provides superior axial strength as compared to a cable or a standard coiled conductor.

The terminal 142 (FIG. 2) is movable with respect to the lead body 113 after the lead 110 has been assembled, and, optionally, after it has been implanted into a heart. The terminal is movable from a first axial position to a second axial position which moves an active fixation assembly 120' at the distal end 114' from a retracted position as shown in FIG. 7, to an extended position as shown in FIG. 8. The distal end 114' of the lead body 113 includes an electrode base 124' which is movably disposed within a bushing 126'. The bushing 126' is sized and configured to receive the electrode base 124' and at least a portion of the inner assembly 160' therein. The bushing 126', in one option, is formed of poly ether ether ketone, for example, by molding. The electrode base 124' is coupled with the inner assembly 160', for example by welding, such that the movement of the terminal 142 (FIG. 2) causes movement of the electrode base 124' and also the active fixation assembly 120'. In one option, as the terminal 142 (FIG. 2) and the inner assembly 160' are rotated, the active fixation assembly 120' is rotated. A surface 127 of the bushing 126 forms a stop for the base 124, and assists in preventing over-extension of the helix (FIG. 2).

FIG. 8 illustrates the distal end 114' of the lead 110' once the terminal 142 (FIG. 4) has been placed in the second axial position. In the second axial position, the fixation helix 122' is extended from the distal end 114' of the lead 110'. In one option, the fixation helix 122' is entirely extended from the lead body 113' in this second axial position (see, for example, FIG. 5). As discussed above, the inner assembly 160' and/or the terminal is used to move the fixation helix 122' axially, without requiring the application of torque to the terminal nor the use of a specialized stylet. Once the fixation helix 122' is extended from the distal end 114' of the lead 110', the terminal 142 (FIG. 2) and/or the inner assembly 160' are rotated, which in turn rotates the fixation helix 122', allowing the lead 110' to be fixated with tissue within a patient.

In another embodiment, a method is provided herein. The method includes pushing on a proximal end of a lead assembly, where the lead assembly has a flexible lead body extending from a proximal end to a distal end, and the lead body including one or more conductors disposed therein. The lead assembly further includes an electrode assembly with at least one electrode electrically coupled with at least one conductor, and a connector assembly coupled with the proximal end of the flexible lead body. The connector assembly has a snap fit terminal having a first position and a second position. The lead assembly further includes an active fixation assembly coupled at the distal end of the flexible lead body. It should be noted that any of the above-discussed lead assemblies could alternatively be used.

The method further includes moving the active fixation assembly axially from an unexposed position to an exposed position, and moving the active fixation assembly is conducted without applying torque to the terminal or the active fixation assembly. In addition, the method includes placing a base of the active fixation assembly in a compression fit with the distal end of the lead body when the active fixation assembly is moved to the exposed position.

Several options for the method are as follows. For instance, in one option, the method further includes removing a clip from the proximal end of the lead body, wherein the clip prevents the terminal from moving between the first position and the second position. In another option, the method includes snap-fittedly coupling the terminal with a terminal housing when the terminal is placed in the second position. The method includes, in another option, rotating the lead body and thereby rotating the active fixation assembly after the active fixation assembly is exposed, or optionally sealing the distal end of the lead body when the active fixation assembly is placed in the exposed position.

In another embodiment, a method comprises pushing on a proximal end of a lead assembly, where the lead assembly has a flexible lead body extending from a proximal end to a distal end, and the lead body has one or more conductors disposed therein. The lead assembly further includes an electrode assembly with at least one electrode electrically coupled with at least one conductor, and a connector assembly coupled with the proximal end of the flexible lead body. The connector assembly includes a terminal movable between a first axial position and a second axial position relative to the lead body after the connector assembly is coupled with the flexible lead body. In addition, the terminal is coupled with a terminal housing in a snap fit connection when the terminal is placed in the second position. The lead assembly further includes an active fixation assembly coupled at the distal end of the flexible lead body, the active fixation assembly including a fixation helix. It should be noted that any of the above-discussed lead assemblies could alternatively be used.

The method further includes moving the terminal from the first axial position to the second axial position, placing the terminal in a snap fit connection with a terminal housing, and pushing the fixation helix from a retracted position to an extended position as the terminal is snap fittedly coupled with the terminal housing. In another option, a snap fit connection is also made at the distal end of the lead along with a snap fit connection at the proximal end of the lead.

Several options for the method are as follows. For instance, in one option, the method further includes placing a base of the active fixation assembly in a compression fit with the distal end of the lead body and sealing the lead body when the active fixation assembly is moved to the exposed position. In another option, the method further includes rotating the lead body and thereby rotating the active fixation assembly after the active fixation assembly is exposed. In yet another option, the method further includes removing a clip from the proximal end of the lead body, wherein the clip prevents the terminal from moving between the first axial position and the second axial position. Additionally, in another option, the method further includes rotating the terminal and thereby rotating the active fixation assembly after the active fixation assembly is placed in the exposed position. In yet another option, the method further includes, disposing a stylet within the lead body, placing a tool member around the stylet, and pushing on the tool member to push the terminal and extend the active fixation assembly from the lead body.

Advantageously, the lead assembly allows for an implant of a lead with the helix disposed within the lead body, which assists in preventing trauma to passages from the helix. In addition, the lead assembly does not require the use of a specialized stylet, which provides a time savings as switching in a specialized stylet involves extra time at implant. In addition, the specialized stylet is disliked by some physicians, and may become a distraction to some physicians. The snap fit terminal assists in locking the fixation assembly in an extended position, eliminating the need to torque the fixation assembly into the extended position, saving time and the uncertainty of whether or how far the fixation assembly has been extended, or preventing the uncertainty of knowing whether a coating over the helix has fully dissolved.

In addition, the snap fit positively indicates to the physician when the helix has been fully extended, and further assists in preventing the helix from inadvertently retreating into the lead body. Furthermore, the snap fit coupling allows for the physician to extend the fixation assembly out to the proper location, and the snap fit coupling positively indicates to the physician when the fixation assembly has been fully and properly extended. The extension of the helix can be done quickly and without trauma to tissue, as opposed to having to wait for a coating to dissolve.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. A lead assembly comprising:
   a flexible lead body extending from a proximal end to a distal end, the lead body including one or more conductors disposed therein;
   an electrode assembly including at least one electrode electrically coupled with at least one conductor;
   a connector assembly coupled with the proximal end of the flexible lead body, the connector assembly including a terminal movable between a first axial position and a second axial position relative to the lead body after the connector assembly is coupled with the flexible lead body;
   an active fixation assembly coupled at the distal end of the flexible lead body, the active fixation assembly placed in a compression fit with the distal end of the lead body when the terminal is placed in the second axial position; and
   an inner assembly coupled with the terminal and the active fixation assembly, where the inner assembly is coupled between the terminal and the active fixation assembly.

2. The lead assembly as recited in claim 1, further comprising a seal disposed at the distal end of the lead body, and the active fixation assembly has a compression fit with the seal at the distal end of the lead body.

3. The lead assembly as recited in claim 1, wherein the terminal has a snap fit coupling with a terminal member when the terminal is placed in the second axial position.

4. The lead assembly as recited in claim 1, wherein the active fixation assembly includes a fixation helix extending outside of the lead body when the terminal is in the second axial position.

5. The lead assembly as recited in claim 4, wherein the entire fixation helix is disposed within the lead body when the terminal is in the first axial position.

6. The lead assembly as recited in claim 1, wherein the active fixation assembly abuts against a stop when the terminal is placed in the second axial position.

7. The lead assembly as recited in claim 1, further comprising a clip coupled with the terminal, where the clip prevents movement of the terminal from the first axial position to the second axial position.

8. A lead assembly comprising:
a flexible lead body extending from a proximal end to a distal end, the lead body including one or more conductors disposed therein;
an electrode assembly including at least one electrode electrically coupled with at least one conductor;
a connector assembly coupled with the proximal end of the flexible lead body, the connector assembly including a terminal movable between a first axial position and a second axial position relative to the lead body after the connector assembly is coupled with the flexible lead body, the terminal coupled with a terminal member in a snap fit connection when the terminal is placed in the second position;
an active fixation assembly coupled at the distal end of the flexible lead body;
an inner assembly coupled with the terminal and the active fixation assembly, where the inner assembly is coupled between the terminal and the active fixation assembly; and
the active fixation assembly includes a fixation helix extending outside of the lead body when the terminal is in the second axial position.

9. The lead assembly as recited in claim 8, wherein the active fixation assembly is placed in a compression fit with the distal end of the lead body when the terminal is placed in the second axial position.

10. The lead assembly as recited in claim 8, wherein the terminal is prevented from being placed in the first axial position once the terminal is placed in the second axial position.

11. The lead assembly as recited in claim 8, further comprising a clip coupled with the terminal, where the clip prevents movement of the terminal from the first axial position to the second axial position.

12. The lead assembly as recited in claim 8, wherein a base coupled with the inner assembly bottoms out against a surface when the terminal is placed in the second axial position.

13. The lead assembly as recited in claim 8, wherein the inner assembly includes an elongate braided member, and the elongate braided member is mechanically coupled with the terminal and the active fixation assembly.

14. The lead assembly as recited in claim 8, wherein the terminal pin is rotatable relative to the lead body after the terminal is placed in the second axial position, and rotation of the terminal pin causes the fixation helix to rotate.

15. The lead assembly as recited in claim 8, further comprising a stylet disposed within the lead body and a tool member disposed over the stylet, the tool member including one or more planar members substantially traverse to a longitudinal axis of the lead body, and axial movement of the tool member causes axial movement to the inner assembly.

16. A lead assembly comprising:
a flexible lead body extending from a proximal end to a distal end, the lead body including one or more conductors disposed therein;
an electrode assembly including at least one electrode electrically coupled with at least one conductor;
a connector assembly coupled with the proximal end of the flexible lead body, the connector assembly including a terminal movable between a first axial position and a second axial position relative to the lead body after the connector assembly is coupled with the flexible lead body;
the terminal having a first snap fit coupling feature and the terminal member having a second snap fit coupling feature, and the first snap fit coupling feature configured to mate with the second snap fit coupling feature when the terminal is placed in the second position;
an active fixation assembly coupled at the distal end of the flexible lead body;
an inner assembly coupled with the terminal and the active fixation assembly, where the inner assembly is coupled between the terminal and the active fixation assembly;
the active fixation assembly includes a fixation helix extending outside of the lead body when the terminal is in the second axial position; and
the terminal pin is rotatable relative to the lead body after the terminal is placed in the second axial position, and rotation of the terminal pin causes the fixation helix to rotate.

17. The lead assembly as recited in claim 16, further comprising a stylet disposed within the lead body and a tool member disposed around at least a portion of an outer circumference of the stylet, the tool member including one or more planar members extending substantially traverse to a longitudinal axis of the lead body, and axial movement of the tool member causes axial movement to the inner assembly.

18. The lead assembly as recited in claim 16, wherein the inner assembly includes an elongate braided member, and the elongate braided member is mechanically coupled with the terminal and the active fixation assembly.

19. The lead assembly as recited in claim 16, wherein the active fixation assembly abuts against a stop when the terminal is placed in the second axial position.

20. The lead assembly as recited in claim 16, wherein the entire fixation helix is disposed within the lead body when the terminal is in the first axial position, and the active fixation assembly includes a fixation helix extending outside of the lead body when the terminal is in the second axial position.

21. A lead assembly comprising:
a flexible lead body extending from a proximal end to a distal end, the lead body including one or more conductors disposed therein;
a connector assembly coupled with the proximal end of the flexible lead body, the connector assembly including a terminal movable between a first axial position and a second axial position relative to the lead body after the connector assembly is coupled with the flexible lead body, a means for coupling the terminal in a snap fit connection with a portion of the lead assembly;

an active fixation assembly coupled at the distal end of the flexible lead body, the active fixation assembly electrically coupled with at least one conductor; and an inner assembly coupled with the terminal and the active fixation assembly, where the inner assembly is coupled between the terminal and the active fixation assembly; and the active fixation assembly includes a fixation helix extending outside of the lead body when the terminal is in the second axial position, and the terminal is coupled with the snap fit connection.

22. The lead assembly as recited in claim 21, wherein a base coupled with the inner assembly bottoms out against a surface when the terminal is placed in the second axial position, and a seal is formed within the distal end when the terminal is placed in the second axial position.

23. The lead assembly as recited in claim 21, wherein the active fixation assembly is placed in a compression fit with the distal end of the lead body when the terminal is placed in the second axial position;

24. The lead assembly as recited in claim 21, wherein the terminal is prevented from being placed in the first position once the terminal is placed in the second position.

25. The lead assembly as recited in claim 21, further comprising a clip coupled with the terminal, where the clip prevents movement of the terminal from the first axial position to the second axial position.

26. A method comprising:

pushing on a proximal end of a lead assembly, the lead assembly having
  a flexible lead body extending from a proximal end to a distal end, the lead body including one or more conductors disposed therein;
  an electrode assembly including at least one electrode electrically coupled with at least one conductor;
  a connector assembly coupled with the proximal end of the flexible lead body, the connector assembly including a snap fit terminal having a first position and a second position; and
  an active fixation assembly coupled at the distal end of the flexible lead body;

moving the active fixation assembly axially from an unexposed position to an exposed position, and moving the active fixation assembly is conducted without applying torque to the terminal or the active fixation assembly; and placing a base of the active fixation assembly in a compression fit with the distal end of the lead body when the active fixation assembly is moved to the exposed position.

27. The method as recited in claim 26, further comprising removing a clip from the proximal end of the lead body, wherein the clip prevents the terminal from moving between the first position and the second position.

28. The method as recited in claim 26, further comprising snap-fittedly coupling the terminal with a terminal member when the terminal is placed in the second position.

29. The method as recited in claim 26, further comprising rotating the lead body and thereby rotating the active fixation assembly.

30. The method as recited in claim 26, further comprising sealing the distal end of the lead body when the active fixation assembly is placed in the exposed position.

31. A method comprising:

pushing on a proximal end of a lead assembly, the lead assembly having
  a flexible lead body extending from a proximal end to a distal end, the lead body including one or more conductors disposed therein;
  an electrode assembly including at least one electrode electrically coupled with at least one conductor;
  a connector assembly coupled with the proximal end of the flexible lead body, the connector assembly including a terminal movable between a first axial position and a second axial position relative to the lead body after the connector assembly is coupled with the flexible lead body, the terminal coupled with a terminal member in a snap fit connection when the terminal is placed in the second position; and
  an active fixation assembly coupled at the distal end of the flexible lead body, the active fixation assembly including a fixation helix;

moving the terminal from the first axial position to the second axial position; and placing the terminal in a snap fit connection with a terminal member, and pushing the fixation helix from a retracted position to an extended position.

32. The method as recited in claim 31, further comprising placing a base of the active fixation assembly in a compression fit with the distal end of the lead body and sealing the lead body when the active fixation assembly is moved to the exposed position.

33. The method as recited in claim 31, further comprising rotating the lead body and thereby rotating the active fixation assembly.

34. The method as recited in claim 31, further comprising removing a clip from the proximal end of the lead body, wherein the clip prevents the terminal from moving between the first axial position and the second axial position.

35. The method as recited in claim 31, further comprising rotating the terminal and thereby rotating the active fixation assembly.

36. The method as recited in claim 31, further comprising disposing a stylet within the lead body, placing a tool member around the stylet, and pushing on the tool member.

* * * * *